United States Patent [19]

Tomita

[11] Patent Number: 5,234,568
[45] Date of Patent: Aug. 10, 1993

[54] APPARATUS FOR SIMULTANEOUS MEASUREMENT OF A PLURALITY OF IONIC CONCENTRATIONS

[75] Inventor: Katsuhiko Tomita, Kyoto, Japan

[73] Assignee: Horiba, Ltd., Kyoto, Japan

[21] Appl. No.: 678,742

[22] Filed: Apr. 1, 1991

[30] Foreign Application Priority Data

Apr. 2, 1990 [JP] Japan ................ 2-35546[U]

[51] Int. Cl.$^5$ ........................................ G01N 27/26
[52] U.S. Cl. .................... 204/416; 204/412;
204/433; 204/435; 204/406; 204/407; 204/418;
204/419
[58] Field of Search .............. 204/416, 418, 407, 406,
204/400, 412, 419, 433, 435

[56] References Cited

U.S. PATENT DOCUMENTS

| 4,225,410 | 9/1980 | Pace | 204/407 |
|---|---|---|---|
| 4,758,325 | 7/1988 | Kanao et al. | 204/412 |
| 4,797,188 | 1/1989 | Tomita | 204/414 |
| 4,816,132 | 3/1989 | Kotani et al. | 204/414 |
| 4,871,439 | 10/1989 | Enzer et al. | 204/412 |
| 4,980,043 | 12/1990 | Tomita et al. | 204/433 |
| 5,024,951 | 6/1991 | Kotani et al. | 204/408 |

Primary Examiner—John Niebling
Assistant Examiner—Bruce F. Bell
Attorney, Agent, or Firm—Price, Gess & Ubell

[57] ABSTRACT

An apparatus for the simultaneous measurement of a plurality of ionic concentrations can utilize a test station having a common support sheet for supporting a plurality of ion selective electrodes, reference electrode and pH responsive electrode. Simultaneous measurements can be taken at the same time from a single sample and the pH reference electrode can validate the operative range of an ion selective electrode.

16 Claims, 7 Drawing Sheets

APPARATUS FOR SIMULTANEOUS MEASUREMENT OF A PLURALITY OF IONIC CONCENTRATIONS

BACKGROUND OF THE INVENTION

1. Field of the Invention

The present invention relates to an apparatus for measuring an ionic concentration in a sample and more particularly to a compact instrument for measuring an ionic concentration having a sheet-type electrode capable of simultaneous measurement of different ions.

2. Description of Related Art

Apparatus for measuring an ionic concentration in a liquid, such as sample solutions, have used so-called sheet-type electrodes for the measurement of ions with an ion selective electrode and a reference electrode formed on the same sheet. With a sheet-type electrode, a measurement of an ionic concentration is possible by the use of a remarkably small quantity of a liquid sample, such as 100 $\mu$l to 1 ml. As a result numerous instruments have been widely used for the measurement of an ionic concentration in various kinds of liquids, including blood.

However, the conventional sheet-type electrode for use in a measurement of ions can measure an ionic concentration of only a single ion and thus it has been necessary in order to provide for the simultaneous measurement of a plurality of kinds of ions that a plurality of sheet-type electrodes for use in the measurement of ions are prepared to carry out an individual measurement. Accordingly, problems have occurred, for example, a liquid to be tested must be individually prepared for every ion to be measured and it is necessary to repeat the measuring operation for each sheet-type electrode for use in a measurement of ions. Thus, the measurement cycle takes excessive time and it is necessary to prepare additional samples of liquid to be tested. Additionally, separate testing procedures can introduce errors, since conditions could vary between each procedure.

SUMMARY OF THE INVENTION

The present invention has been achieved in response to the above described matters and it is an object of the present invention to provide an instrument for simultaneously measuring ionic concentrations of a plurality of kinds of ions within a single sample.

In order to achieve the above described object, an apparatus for measuring ionic concentrations, according to the present invention, is characterized in that a reference electrode and a plurality of kinds of ion selective electrodes are formed on the same electrode sheet. Additionally, a pH-measuring electrode may also be used as one of the plurality of kinds of ion selective electrodes.

With an apparatus for measuring an ionic concentration having the above described characteristic construction, concentrations of a plurality of different types of ions can be measured by merely providing a drop of sample liquid to be tested on a pre-determined surface of the sheet and thus the measuring operation time and the quantity of the sample liquid to be tested can be remarkably reduced.

Finally, when a pH-measuring electrode is used as one of the possible plurality of kinds of ion selective electrodes, then a calibration of ionic concentrations can be measured at the same time.

BRIEF DESCRIPTION

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

One preferred embodiment of the present invention is shown in FIGS. 1 to 4, in which FIG. 1 is a perspective view showing one preferred embodiment of an apparatus for measuring ionic concentrations according to the present invention;

DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein specifically to provide a compact measuring instrument that can measure a number of different ionic concentrations and pH at one test site.

The preferred embodiments of the present invention will be below described with reference to the drawings.

Figure 1:
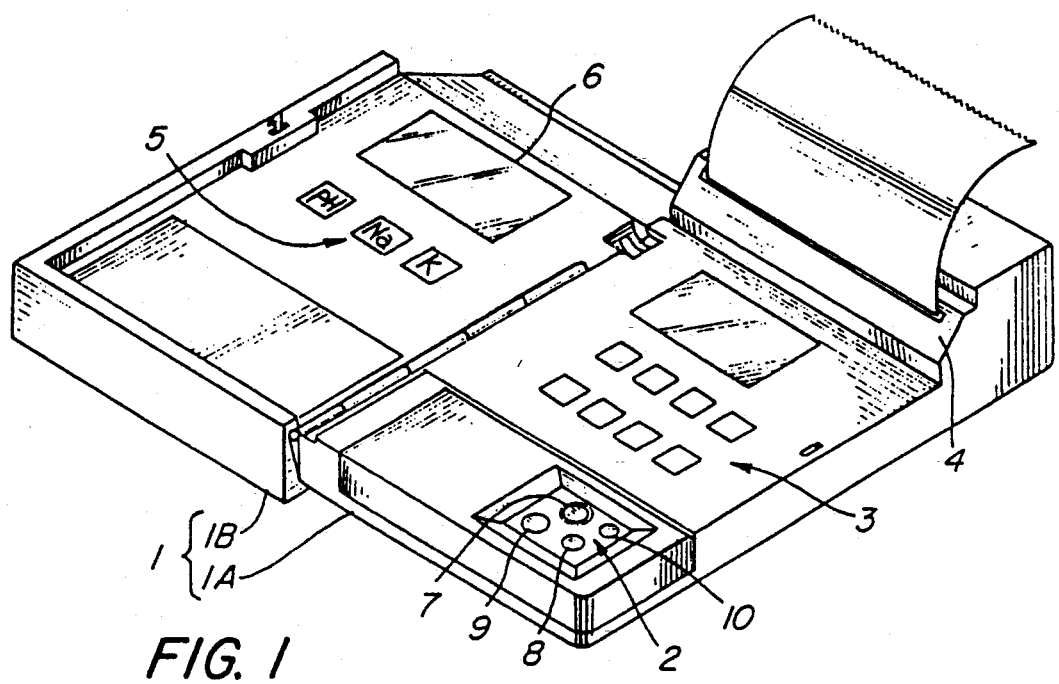

One preferred embodiment of the present invention is shown in FIGS. 1 to 4, in which FIG. 1 shows a card size pocket calculator-type apparatus for measuring ionic concentrations. A bifurcated body case comprising one member case 1A is provided with a measuring station or test portion 2, an operational key board 3, and a printer 4 and the other member case 1B is provided with a display-selecting key 5 and a display panel 6. The respective case members 1A and 1B can be folded together for storing purposes. The case 1 can be provided with a micro computer capacity for carrying out an operational treatment of the ion measurements, a memorization of test measurements and the like. The printer 4 can provide a hard copy of the rest results. Additionally, the microcomputer can be programmed to validate the operative range of ionic measurements by comparison with a simultaneous pH measurement.

Figure 2:
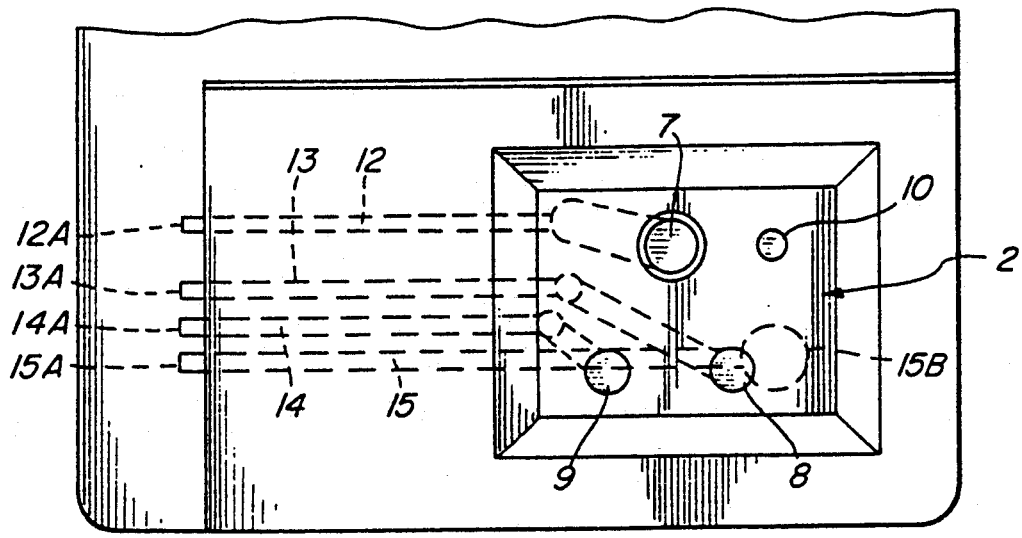
FIG. 2 is an enlarged plan view showing the main component parts of the apparatus for measuring ionic concentrations according to the present invention shown in FIG. 1.

The measuring portion 2 is provided with a measuring electrode 7, a $Na^+$-measuring electrode 8, a $K^+$-measuring electrode 9 and a reference electrode (liquid junction) 10 which is used for each of the respective measuring electrodes, 7, 8, 9. These electrodes are provided on a common support sheet, as shown in FIG. 2.

Figure 3:
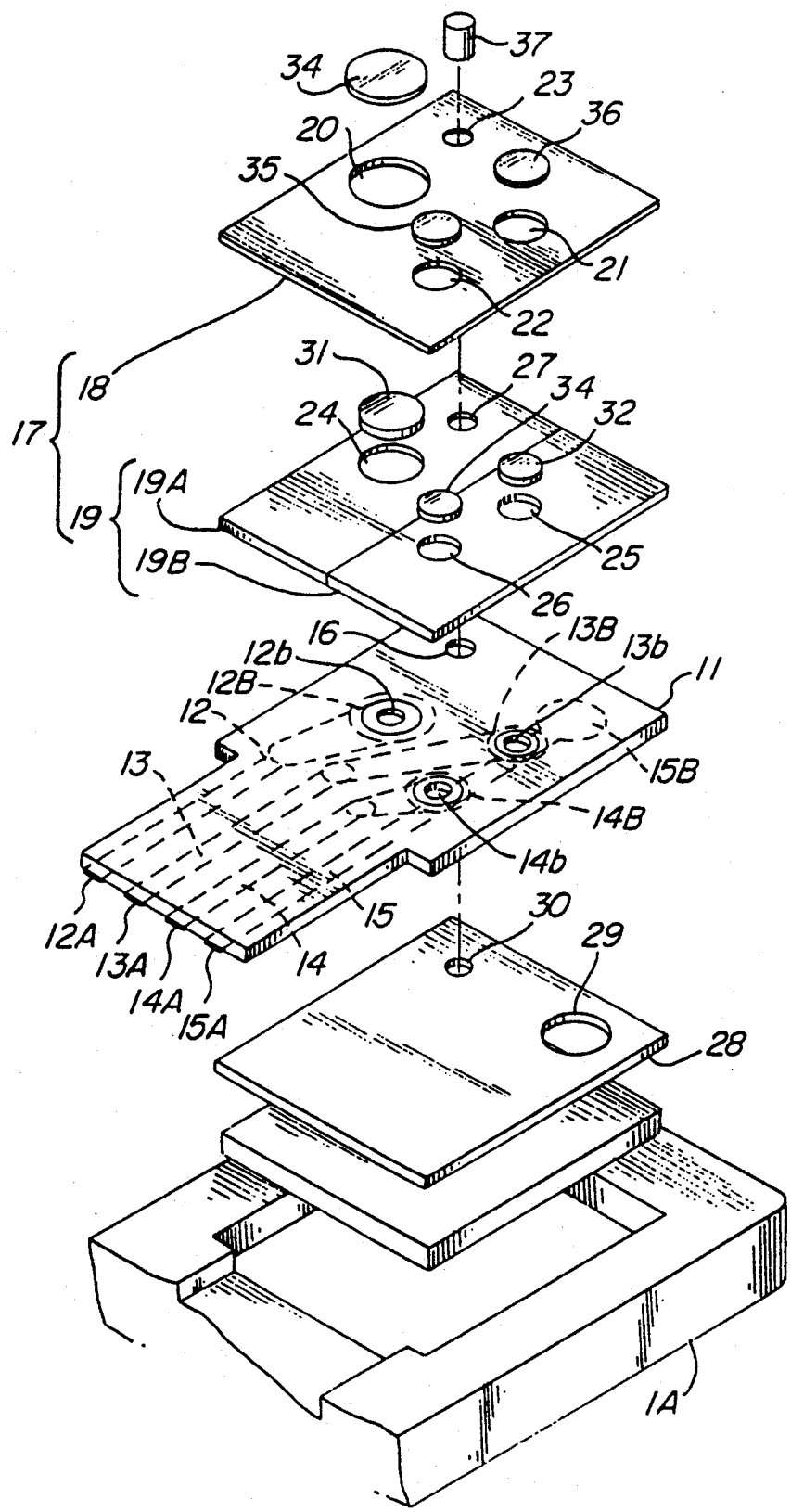
FIG. 3 is an exploded perspective view showing the main parts of a measuring portion or testing station.
Figure 4:
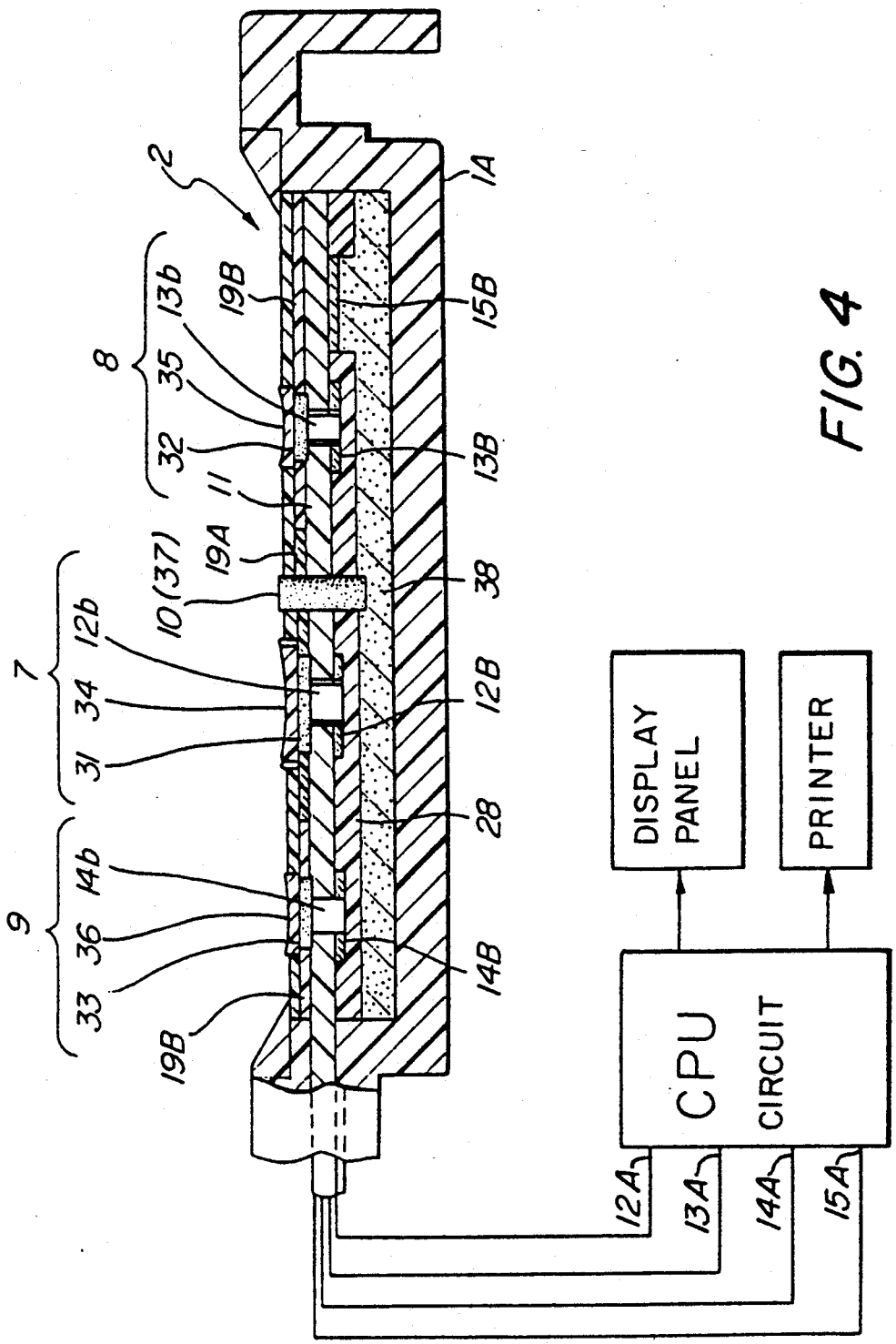
FIG. 4 is a partial cross-sectional view showing the main parts of the measuring portion shown in FIG. 3 and a schematic diagram of the computational circuit.

Next, a construction of the main parts of the measuring portion 2 is described with reference to FIGS. 3 and 4. Reference numeral 11 designates an insulating substrate formed of a material having a sufficiently high insulation capacity even though it is immersed in a solution containing an electrolyte, such as polyethylene terephthalate (hereinafter referred to as PET). The insulating substrate 11 is provided with four electrodes 12, 13, 14, 15 that are formed on a lower surface thereof by subjecting the substrate 11 to a grafting treatment and an anchoring treatment with a silane coupling agent followed by silk-screening of an Ag paste to form the dotted conductive electrode leads.

Portions of the electrode leads extending in a direction towards one end of the insulating substrate 11 are used as lead portions 12A, 13A, 14A, 15A, while portions positioned on the central side of the insulating substrate 11 are formed in, for example, a circular shape to coat the circular portions with an electrode material, such as AgCl, thereby forming internal electrode portions 12B, 13B, 14B, 15B. Internal electrode portions 12B, 13B, 14B (excepting the internal electrode portion 15B) are provided with a through hole $12a$, $13a$, $14a$ having electrically conductive portions formed at an almost center thereof, respectively, while the internal electrode portion 15B is provided with a through hole 16 formed in the vicinity thereof. In addition, as is clear from a description to be mentioned later, the internal electrode portion 12B, 13B, 14B corresponds to the Na+ measuring electrode 7, the $NO^{3-}$ measuring electrode 8 and the pH-measuring electrode 9, respectively. The through hole 16 serves as the common liquid junction 10 of the reference electrode for the respective measuring electrodes 7, 8, 9. The internal electrode portion 15B is further connected with a liquid junction portion 37 through a gelatinized internal liquid 38.

Reference numeral 17 designates a double-structured insulating support layer provided on one side of an upper surface of the insulating substrate 11. The double-structured insulating support layer 17 comprises an upper sheet material 18 made of PET and a combined lower sheet material 19 made of PET 19A and PVC 19B so that it is provided with a sufficiently high insulation characteristic even though it is immersed in a solution containing an electrolyte in the same manner as the insulating substrate 11. The lower sheet material 19 comprises two separate sheets 19A, 19B having the same size (equal in surface area and thickness) and arranged in parallel, the PET sheet 19A is positioned so as to face the internal electrode portion 12B and the through hole 16, while the PVC sheet 19B is positioned so as to face the internal electrode portions 13B, 14B. The insulating support layer 17 is formed by, for example, subjecting splicing surface sides of both sheet materials 18, 19 to a preliminary surface treatment of printing by the use of an ultraviolet setting ink and a semi-drying operation followed by pressing both sheet materials 18, 19 against each other.

The upper sheet material 18 is provided with circular through holes 20, 21, and 22 having an appointed size and formed at positions corresponding to the internal electrode portions 12B, 13B, 14B and a through hole 23 having the same diameter as that of the through hole 16 formed at a position corresponding to the through hole 16. In the lower sheet material 19, the PET sheet 19A is provided with a circular through hole 24 slightly smaller than the through hole 20 and formed at a position corresponding to the through hole 20 and a through hole 27 having the same diameter as that of the through hole 23 and also formed at a position corresponding to the through hole 23. In addition, the PVC sheet 19B is provided with through holes 25 and 26, each slightly smaller than the through holes 21 and 22, respectively, at positions corresponding to the through holes 21 and 22, respectively.

Furthermore, an upper surface of the upper sheet material 18 is also subjected to a grafting process and an anchoring treatment by the use of a silane coupling agent and the like.

Reference numeral 28 designates a lower support layer provided on a side of a lower surface of the insulating substrate 11. The lower support layer 28 is made of PET so that it may have a sufficiently high insulation characteristic, even though it is immersed in a solution containing an electrolyte in the same manner as the insulating substrate 11 and the insulating support layer 17 and it is further provided with a through hole 29 and a through hole 30 formed at positions corresponding to the internal electrode portion 15B and the through hole 16 formed in the insulating substrate 11, respectively. In addition, a through hole 30 is formed so as to have the same diameter as that of the through hole 16.

Reference numerals 31, 32, 33 designate a solidified gelatinized internal liquid made of, for example, (0.03M-$KNO_3$-0.1M-KCl)-glycerine-agar-agar and formed in a disk-like shape when filled into the through holes 24, 25 and 26 that are pre-formed in the lower sheet material 19 The gelatinized disks 31, 32, and 33 are initially turned into a paste like substance by heating and then the paste is filled into the respective through holes 24, 25, and 26 by a screen printing method under a condition that their upper surfaces are slightly below the upper surface of the upper sheet material 18 and they are also connected with the internal electrode portions 12B, 13B, 14B through the electrically conductive portions within the through holes $12b$, $13b$, $14b$ formed in the insulating substrate 11.

Reference numeral 34 designates a pH glass responsive membrane, which is responsive only to H+. The glass electrode is provided on an upper surface of the gelatinized internal liquid 31 to form the pH-measuring electrode 7.

Reference numeral 35, 36 designates a PVC liquid membrane-type ion responsive membrane provided on an upper surface of the gelatinized internal liquid disks 32, 33, respectively. In the present preferred embodiment, the responsive membrane 35 is selectively responsive to a Na+ and the responsive membrane 36 is selectively responsive to K+. An ion responsive substance containing membrane paste is inserted drop by drop into the gelatinized internal liquid 32, 33, respectively, to form and Na+-measuring electrode 8 and the K+-measuring electrode 9.

For example, in order to prepare the responsive membrane 35 of the Na+-measuring electrode 8, $B$is-12-Crown-4 as the responsive substance to Na+, PVC powders and di-n-octyl phthalate (n-DOP) as a plasticizer are dissolved in tetrahydrofuran as a solvent in an appointed quantity, respectively, to obtain the responsive membrane paste and the obtained responsive membrane paste is inserted drop by drop into the gelatinized internal liquid 32 from above by means of, for example, a syringe. In addition, in order to prepare the responsive membrane 36 of the K+-measuring electrode 9, barinomycin as the responsive substance to K+ and di-n-octyl phthalate (n-DOP) as a plasticizer are dissolved in tetrahydrofuran as a solvent in an appointed quantity, respectively, to obtain the responsive membrane paste and the obtained responsive membrane paste is inserted drop by drop into the gelatinized internal liquid 32 from above by means of a syringe.

Reference numeral 37 designates a gel-impregnated hydrophilic high molecular porous member as a liquid junction of the reference electrode 10 provided so as to be inserted through the through holes 23, 27, 16, 30 formed at corresponding positions of the upper sheet material 18, the lower sheet material 19A, the substrate 11 and the lower support layer 28. The gel-impregnated hydrophilic high molecular porous member 37 is made of a sintered molded body of olefin family high polymer powders (for example, Sun Fine AQ [trade name] made by Asahi Kasei KK) having a mechanical strength nearly the same as that of polyoelfines and a hydrophilicity provided by a denaturing treatment impregnated with a so-called undrying out gel composite, which deposits no KCl and does not lose a wetness characteristic of a surface of the porous member after exposure in air, for example, a water-containing jelly mainly comprising a Na salt of an acrylic polyerm (for example, U jelly [trade name] made by Showa Denko KK), and provided so as to slightly project over the surface of the support layer 10.

Reference numeral 38 designates a gelatinized internal liquid mainly comprising $NH_4Cl$ adapted not only to be brought into contact with the internal electrode portion 15B formed in the insulating substrate 11 through the through hole 29 formed in the lower support layer 16 but also to be brought into contact with the gel-impregnated hydrophilic high molecular porous member 37.

With an apparatus for measuring an ionic concentration having the above described construction, the concentrations of $Na^+$ and $K^+$ and the pH in the liquid to be tested can be simultaneously measured by merely providing only one drop of the sample liquid to be tested on the measuring portion 2 and an appointed ionic concentration can be displayed on the display panel 6 by suitably selecting and pushing a corresponding key in the display-selecting key panel 5.

As understood from the above described preferred embodiment, the insulating substrate 11 is provided with the double-structured insulating support layer 17 formed on the side of the upper surface of the substrate 11, the upper sheet material 18 being made of PET, the lower sheet material 19 being made of PET 19A and PVC 19B. The PET sheet 19A is further provided with a glass electrode responsive membrane (the $H^+$ glass responsive membrane 34 in the above described preferred embodiment), and the PVC sheet 19B is provided with the PVC liquid membrane-type ion responsive membranes (the $Na^+$ ion responsive membrane 35 and the $K^+$ responsive membrane 36 in the above described preferred embodiment).

In summary, the glass responsive membrane is preferably used as the ion responsive membrane 34 provided on the PET sheet 19A and the PVC liquid membrane-type ion responsive membrane is preferably used as the ion responsive membranes 35, 36 provided on the PVC sheet 19B. Accordingly, also a $Na^+$ glass responsive membrane and a single crystalline $F^-$ responsive membrane may be used in addition to the above described $H^+$ glass responsive membrane.

The measuring electrodes may be further optionally combined. Although it is not shown, the PET sheet 19A may be provided with the $Na^+$-measuring electrode and the PVC sheet 19B may be provided with the pH-measuring electrode and a $NO_3^-$ measuring electrode so that the concentrations of $Na^+$ and $NO_3^-$ and the pH can be simultaneously measured. In this case, for the $H^+$ responsive membrane, trioctylphosphine oxide is used as the responsive substance, and PVC powders and o-nitrophenyloctyl ether as the plasticizer material are dissolved in tetrahydrofuran as a solvent in an appointed quantity to obtain the responsive paste. The obtained responsive paste is inserted drop by drop in the same manner as described above. In addition, as for the $NO_3^-$ responsive membrane, tetraoctylammonium nitrate, which is a nitrate-type quaternary ammonium salt ($RNNO_3$, R: $C_8$ to $C_{17}$), is used as the $NO_3^{31}$ responsive substance, and tetraoctylammonium nitrate PVC powders and di-n-octyl phthalate as the plasticizer are dissolved in tetrahydrofuran as the solvent in the appointed quantity to obtain the responsive paste and the obtained responsive paste is applied in a drop by drop method. In addition, it is sufficient that the gelatinized internal liquid 38 on the side of the reference electrode 10 is mainly made of lithium acetate. Furthermore, the pH and $Ca^{++}$ may be simultaneously measured.

Figure 5:
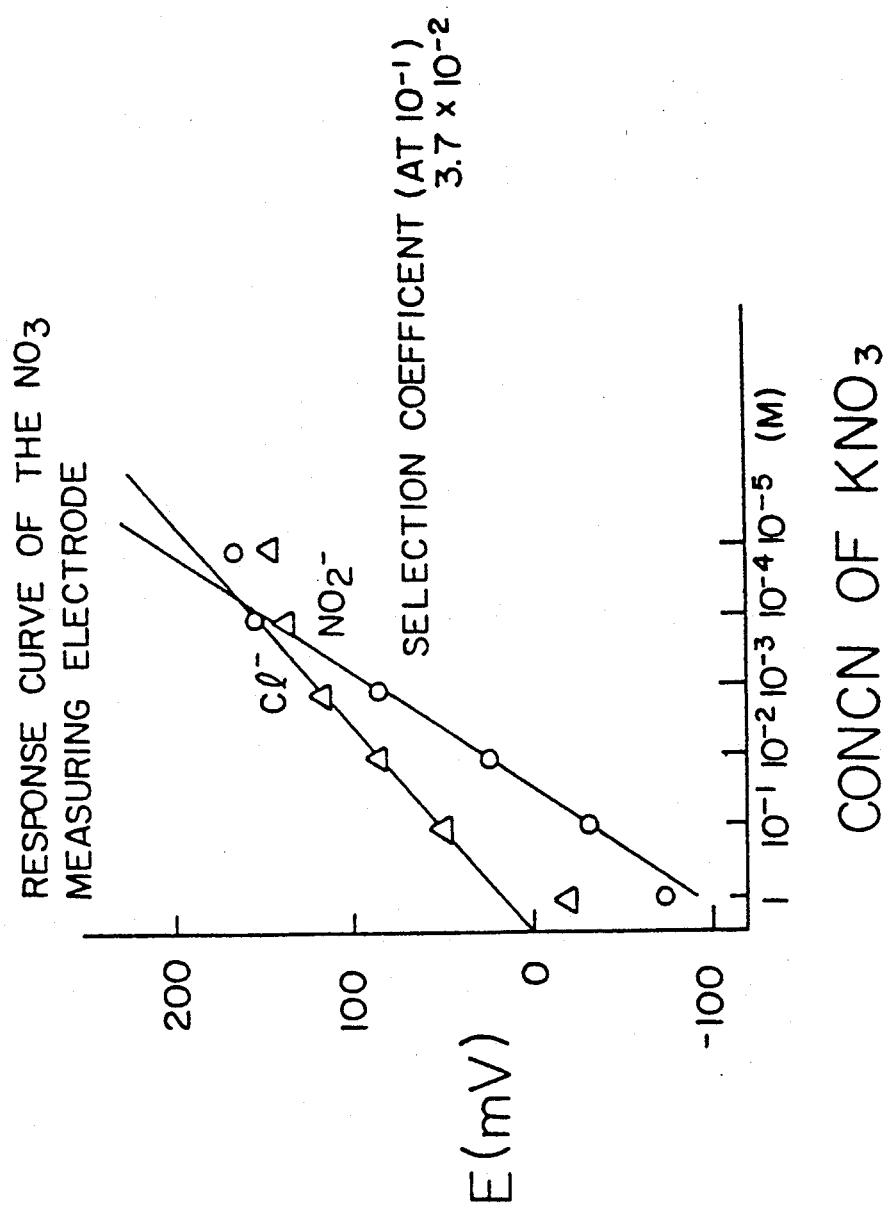
FIGS. 5 to 7 are diagrams showing response curves of measuring electrodes.
Figure 6:
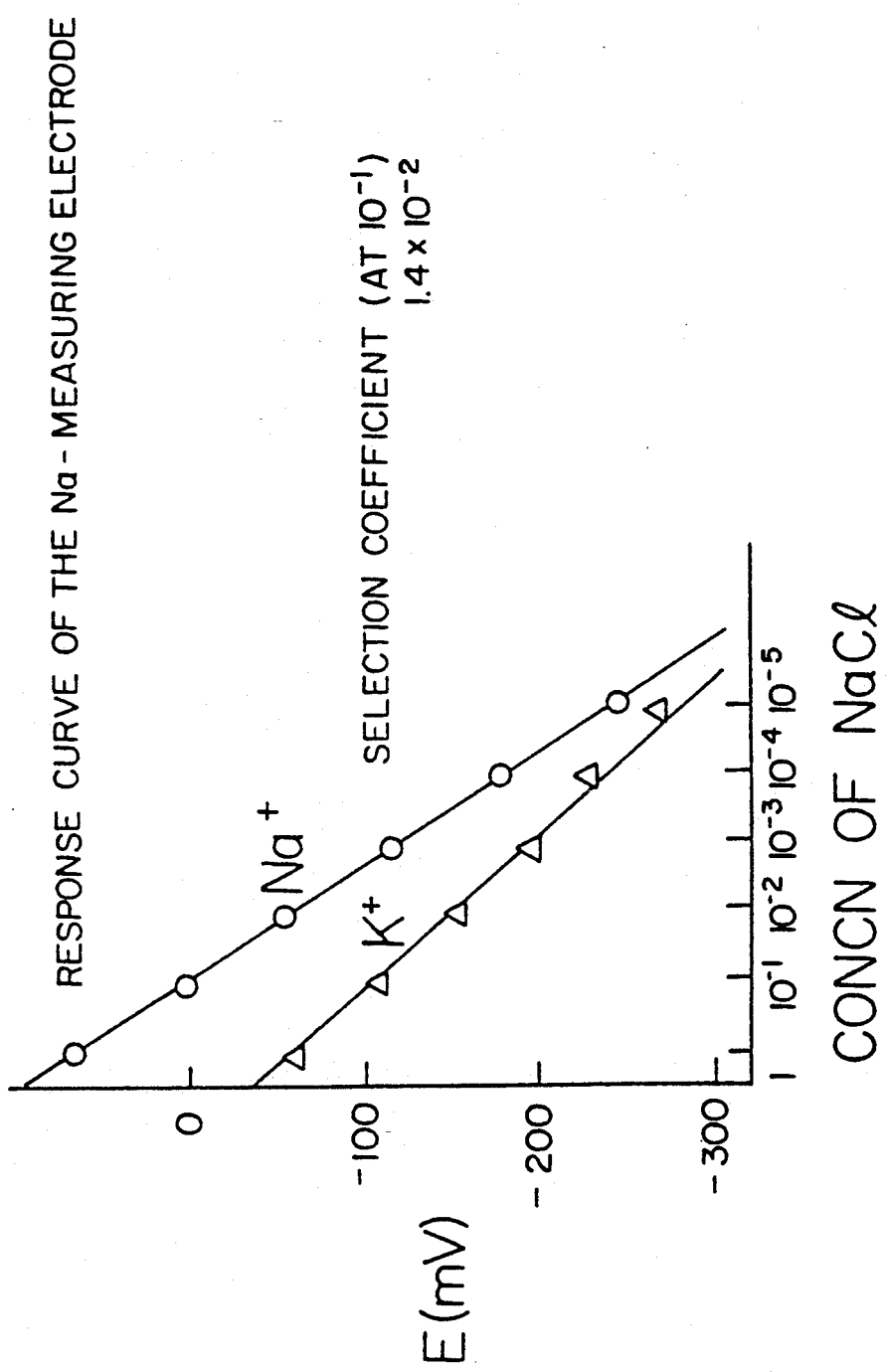
Figure 7:
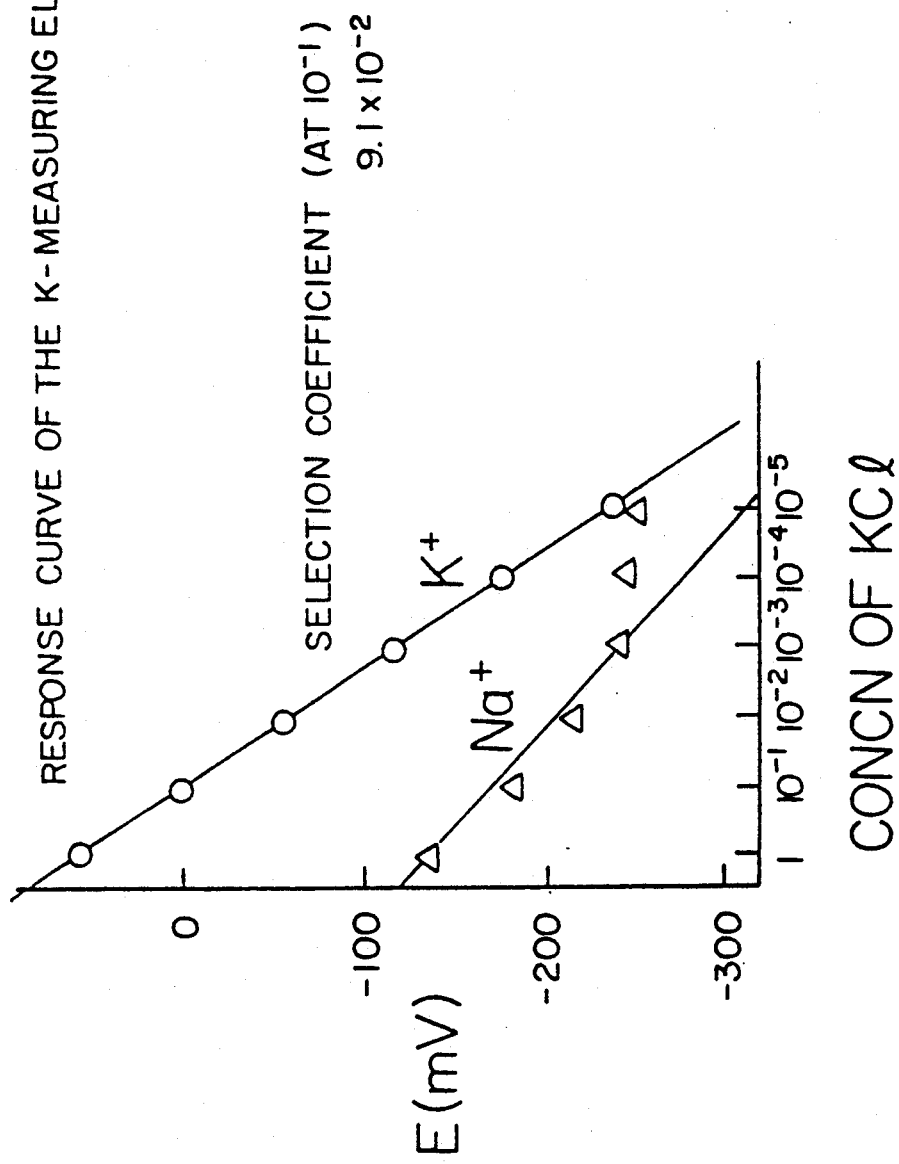

FIG. 5 to 7 show response output curves of the $Na^+$-measuring electrode, the $K^+$-measuring electrode and the $NO_3^-$-measuring electrode, respectively, versus a concentration level of the sample.

For example, in an apparatus for measuring an ionic concentration capable of simultaneously measuring the concentrations of $Na^+$ and $K^+$ and the pH, provided that selection coefficients on the basis of mutual interferential characteristics of $Na^+$ and $K^+$ are $K_{Na}$ and $K_K$, indicated values by the $Na^+$-measuring electrode and the $K^+$-measuring electrode being $S_{Na}$ and $S_K$, and true concentration values of $Na^+$ and $K^+$ being $[X_{Na}]$ and $[Y_K]$, the following simultaneous equations hold good:

$$S_{Na} = [X_{Na}] + K_{Na}[Y_K]$$

$$S_K = [Y_K + K_K[X_{Na}]$$

Thus, true values $X_{Na}$, $Y_K$ can be calibrated in a range of low concentrations of $10^{-4}$ to $10^{-7}$M and thus a highly accurate measurement can be achieved by resolving these equations by means of a micro computer included in the apparatus. The simultaneous equations address the interferential characteristics that the Na-ion electrode is responsive to not only an Na-ion but also a K-ion. As can be seen in FIG. 4, the computer based circuits can solve the equations and provide a readout on either the display panel and/or the printer.

Figure 8:
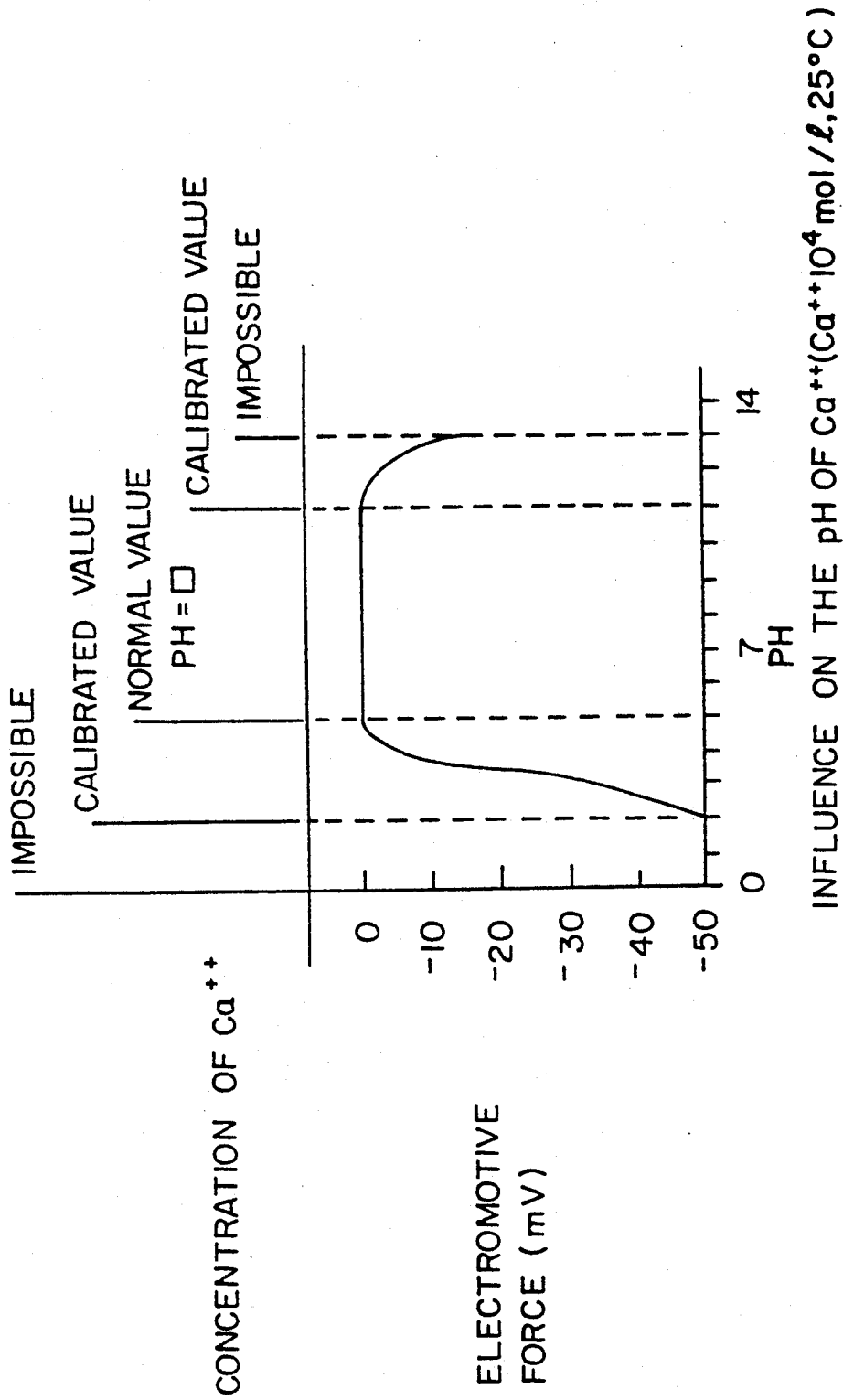
FIG. 8 is a graph showing an influence of the pH in a measurement of a concentration of $Ca^{++}$.

FIG. 8 is an empirically derived graph showing an influence of pH upon the measurement of concentration of $Ca^{++}$. In FIG. 8, the change of an electrode output relative to pH is shown under the condition that the concentration of the Ca-ion is $10^{-4}$ mol/l and the temperature is 25° C. The reason why the output is changed is not fully understood but it appears that the responsive substance of the Ca-ion electrode is influenced by the level of pH. It is also possible that a precipitation in the form of $Ca(OH)_2$ has an effect in the case where the value of pH is increased. It can be found from FIG. 8 that the measuring condition of the $Ca^{++}$-measuring electrode can be indicated as a normal range, a calibrated calculation range and an impossible calculation range on the basis of the indicated value of pH. In FIG.

8, the pH range of 5 to 11 is a range showing normal values, the pH ranges of 2 to 5 and 11 to 13 are ranges where calibration can be achieved, and the pH ranges of 0 to 2 and 13 to 14 are the ranges where the calibration cannot be achieved. However, if the above described conditions are changed, the curve can also be changed in form. For example, the range of normal values can be reduced in width with a reduction of the concentration of Ca-ions. If desired, the computer can also be programmed to validate ionic concentration on the basis of the pH measurement in accordance with the values of a curve, such as FIG. 8.

As above described, according to the present invention, a plurality of ionic concentrations can be measured by merely inserting one drop of liquid to be tested on the sheet and thus the complexity of the measuring operation and the amount of liquid to be tested can be remarkably reduced. In the case where the pH-measuring electrode is also used as one of a plurality of kinds of ion selective electrodes, the ionic concentration, which is measured at the same time, can be also be calibrated or validated on the basis of the same results of measurement.

Accordingly, a plurality of kinds of ionic concentration can be simultaneously measured with high accuracy.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. An instrument for measuring an ionic concentration in a sample, including:

a housing member;

a testing station on the housing member defining an open common receptacle for receiving the sample, a bottom surface of the receptacle supporting a plurality of ion-selective electrodes for measuring a plurality of different ionic concentrations in the sample when it is deposited in the common receptacle, a pH-responsive electrode, and a single common reference electrode for providing an output relative to each of the ion-selective electrodes, the testing station further including a single sheet member supporting the reference electrode, the ion-selective electrodes, and pH-responsive electrode, and means, in the housing member, for computing the amount of ionic concentration based on the output of, respectively, the pH-responsive electrode, at least one of the ion-selective electrodes, and the reference electrode.

2. The invention of claim 1, wherein the housing member is split into a first case member and a second case member that are pivotally attached, wherein the first case member can be folded into a storage position above the second case member and opened to be positioned adjacent the first case member to expose the testing station for operation.

3. The invention of claim 1 wherein the single sheet member is divided into an upper and lower layer.

4. The invention of claim 1 wherein the ion-selective electrodes include an $Na^+$ electrode and an $NO^{3-}$ electrode.

5. The invention of claim 3 wherein the lower layer is split into a first sheet portion of polyethylene terephthalate and a second sheet portion of polyvinyl chloride.

6. The invention of claim 5, further including means for validating an ionic concentration range based on a simultaneous output of the pH-responsive electrode.

7. The invention of claim 5, wherein each electrode includes a disk-shaped solid gelatinized internal liquid.

8. The invention of claim 5 wherein an $Na^+$-measuring electrode is provided with a membrane of a solidified PVC liquid on the polyethylene terephthalate first sheet portion.

9. The invention of claim 6 wherein the ionic concentration range is for $Ca^{++}$.

10. A compact instrument for simultaneous measurement of a plurality of ionic concentrations in a static sample, comprising:

a bifurcated housing member having a first case member and a second case member pivotally attached to fold together, with the first case member positioned above the second case member for storage purposes and opened to position the first case member alongside the second case member for measurement operations;

a display panel in the housing member;

key means for activating the display panel;

a testing station on the housing member including an open common receptacle for receiving the sample having a common reference electrode, a plurality of ion-selective electrodes for measuring a plurality of different ionic concentrations, a pH-responsive electrode, and a single sheet member supporting the reference electrode, the pH-responsive electrode and the ion-selective electrodes for forming a bottom surface of the common receptacle;

means for computing the amount of ionic concentration for display on the display panel; and means for validating an ionic concentration measured by an ion-selective electrode based on an output of the pH-responsive electrode.

11. The invention of claim 10, further including a printer on the housing member for providing a printout of the measurements.

12. An instrument for measuring an ionic concentration in a sample, including:

a housing member;

a testing station on the housing member defining an open common receptacle for receiving the sample, a bottom surface of the receptacle supporting a plurality of ion-selective electrodes for measuring a plurality of different ionic concentrations, a pH-responsive electrode, and a common reference electrode for each of the ion-selective electrodes, the testing station further including a sheet member supporting the reference electrode, ion-selective electrodes, and pH-responsive electrode, and means in the housing member for computing the amount of ionic concentration and displaying the amount to an operator.

13. The invention of claim 12, wherein the housing member is split into a first case member and a second case member that are pivotally attached, wherein the first case member can be folded into a storage position above the second case member and opened to be positioned adjacent the first case member to expose the testing station for operation.

14. The invention of claim 12 wherein the sheet member is divided into an upper and a lower layer.

15. The invention of claim 12 wherein the ion-selective electrodes include an $Na^+$ electrode and an $NO^{3-}$ electrode.

16. The invention of claim 14 wherein the lower layer is split into a first sheet portion of polyethylene terephthalate and a second sheet portion of polyvinyl chloride.

* * * * *